United States Patent
Wang et al.

(10) Patent No.: US 11,931,208 B2
(45) Date of Patent: Mar. 19, 2024

(54) CEREBRAL PERFUSION STATE CLASSIFICATION APPARATUS AND METHOD, DEVICE, AND STORAGE MEDIUM

(71) Applicant: BEIJING FRIENDSHIP HOSPITAL, CAPITAL MEDICAL UNIVERSITY, Beijing (CN)

(72) Inventors: Zhenchang Wang, Beijing (CN); Wei Zheng, Beijing (CN); Han Lv, Beijing (CN); Pengling Ren, Beijing (CN); Dehong Luo, Beijing (CN); Linkun Cai, Beijing (CN); Yawen Liu, Beijing (CN); Hongxia Yin, Beijing (CN); Pengfei Zhao, Beijing (CN); Jing Li, Beijing (CN); Dong Liu, Beijing (CN); Erwei Zhao, Beijing (CN); Tingting Zhang, Beijing (CN)

(73) Assignee: BEIJING FRIENDSHIP HOSPITAL, CAPITAL MEDICAL UNIVERSITY, Beijing (CN)

(*) Notice: Subject to any disclaimer, the term of this patent is extended or adjusted under 35 U.S.C. 154(b) by 0 days.

(21) Appl. No.: 17/749,864

(22) Filed: May 20, 2022

(65) Prior Publication Data
US 2023/0125247 A1 Apr. 27, 2023

(30) Foreign Application Priority Data
Aug. 17, 2021 (CN) .......................... 202110943317.9

(51) Int. Cl.
*A61B 8/08* (2006.01)
*A61B 5/00* (2006.01)
(Continued)

(52) U.S. Cl.
CPC .......... *A61B 8/5223* (2013.01); *A61B 5/0042* (2013.01); *A61B 5/0263* (2013.01);
(Continued)

(58) Field of Classification Search
None
See application file for complete search history.

(56) References Cited

U.S. PATENT DOCUMENTS

2006/0265022 A1* 11/2006 John ...................... A61N 2/006
607/45
2011/0211742 A1* 9/2011 Bredno .................. A61B 6/481
382/128

(Continued)

FOREIGN PATENT DOCUMENTS

CN 113569984 A 10/2021

OTHER PUBLICATIONS

Canadian Examination report dated Nov. 1, 2022 as received in application No. 3,159,995.
(Continued)

*Primary Examiner* — Jonathan Cwern
(74) *Attorney, Agent, or Firm* — Maschoff Brennan

(57) ABSTRACT

The present application discloses a cerebral perfusion state classification apparatus and method, a device, and a storage medium. The method includes: acquiring, by a transceiving module, cervical blood flow data from an ultrasound data collecting device; determining, by a processor, cerebral perfusion data corresponding to the cervical blood flow data based on the cervical blood flow data and a mapping relationship between the cervical blood flow data and the cerebral perfusion data, and classifying cerebral perfusion states of a plurality of brain regions based on blood perfusion characteristics of the plurality of brain regions in the cerebral perfusion data.

8 Claims, 4 Drawing Sheets

(51) Int. Cl.
*A61B 5/026* (2006.01)
*A61B 5/055* (2006.01)
*A61B 8/06* (2006.01)
*G16H 30/40* (2018.01)
*G16H 50/50* (2018.01)

(52) U.S. Cl.
CPC ............... *A61B 5/055* (2013.01); *A61B 8/06* (2013.01); *A61B 8/5261* (2013.01); *G16H 30/40* (2018.01); *G16H 50/50* (2018.01)

(56) References Cited

U.S. PATENT DOCUMENTS

| | | | | |
|---|---|---|---|---|
| 2011/0282169 | A1* | 11/2011 | Grudic | G16H 50/50 600/371 |
| 2019/0150764 | A1* | 5/2019 | Arnold | G06V 10/82 |
| 2022/0172040 | A1* | 6/2022 | Kazi | G06N 3/08 |

OTHER PUBLICATIONS

Chinese Office Action dated Dec. 15, 2021 as received in application No. 202110943317.9.

* cited by examiner

CEREBRAL PERFUSION STATE CLASSIFICATION APPARATUS AND METHOD, DEVICE, AND STORAGE MEDIUM

FIELD

The present application belongs to the technical field of computers, and particularly relates to a cerebral perfusion state classification apparatus and method, a device, and a storage medium.

BACKGROUND

Cerebral perfusion imaging is mainly used to reflect a blood perfusion state of a brain tissue. In related technologies, large devices, such as computed tomography (CT) and magnetic resonance imaging (MRI), are often used for examination, and then, cerebral blood flow and a cerebral functional state are evaluated according to examination results.

However, in related technologies, the examination devices with complicated operation and large size are inapplicable to some special scenarios, such as aerospace scenarios and outdoor emergency scenarios. Therefore, a new solution is to be proposed.

SUMMARY

In view of the above, the present application provides a cerebral perfusion state classification apparatus and method, a device, and a storage medium to solve or partially solve the above technical problems.

In a first aspect, embodiments of the present application provide a cerebral perfusion state classification apparatus, which includes:
  a transceiving module, configured to acquire cervical blood flow data from an ultrasound data collecting device; and
  a processor, configured to determine cerebral perfusion data corresponding to the cervical blood flow data based on the cervical blood flow data and a mapping relationship between the cervical blood flow data and the cerebral perfusion data; and
  further configured to classify cerebral perfusion states of a plurality of brain regions based on blood perfusion characteristics of the plurality of brain regions in the cerebral perfusion data.

Optionally, when determining cerebral perfusion data corresponding to the cervical blood flow data based on the cervical blood flow data and a mapping relationship between the cervical blood flow data and the cerebral perfusion data, the processor is specifically configured to:
  extract cervical blood flow characteristics from the cervical blood flow data; and
  input the cervical blood flow characteristics into a pretrained network model to obtain cerebral perfusion data corresponding to the cervical blood flow characteristics,
  wherein the network model is trained based on cervical blood flow characteristic samples and cerebral perfusion data samples.

Optionally, the processor is further configured to:
  receive a brain magnetic resonance image obtained by arterial spin labeling;
  divide the brain magnetic resonance image into a plurality of brain regions; and
  take cerebral perfusion data of each of the plurality of brain regions as a cerebral perfusion data sample.

Optionally, the network model includes: a deep learning model constructed based on long short-term memory (LSTM); and the deep learning model includes: a Seq2Seq model including an encoder and a decoder.

Optionally, when classifying cerebral perfusion states of a plurality of brain regions based on blood perfusion characteristics of the plurality of brain regions in the cerebral perfusion data, the processor is specifically configured to:
  extract blood perfusion characteristics of a plurality of brain regions from the cerebral perfusion data; and
  determine a cerebral perfusion state type to which each of the plurality of brain regions belongs based on the blood perfusion characteristics and blood perfusion characteristic thresholds corresponding to cerebral perfusion state types.

Optionally, the blood perfusion characteristics include cerebral blood flow. The processor is further configured to:
  set cerebral blood flow thresholds corresponding to the cerebral perfusion state types.

Optionally, the cervical blood flow data include one or a combination of cervical vessel blood flow data and vascular lumen morphology change data.

In a second aspect, embodiments of the present application provide a cerebral perfusion state classification method, which includes:
  acquiring cervical blood flow data from an ultrasound data collecting device;
  determining cerebral perfusion data corresponding to the cervical blood flow data based on the cervical blood flow data and a mapping relationship between the cervical blood flow data and the cerebral perfusion data; and
  classifying cerebral perfusion states of a plurality of brain regions based on blood perfusion characteristics of the plurality of brain regions in the cerebral perfusion data.

In a third aspect, embodiments of the present application provide an electronic device, which includes: a memory and a processor, wherein
  the memory is configured to store a program; and
  the processor is coupled with the memory and configured to execute the program stored in the memory so as to:
  acquire cervical blood flow data from an ultrasound data collecting device;
  determine cerebral perfusion data corresponding to the cervical blood flow data based on the cervical blood flow data and a mapping relationship between the cervical blood flow data and the cerebral perfusion data; and
  classify cerebral perfusion states of a plurality of brain regions based on blood perfusion characteristics of the plurality of brain regions in the cerebral perfusion data.

In a fourth aspect, embodiments of the present application provide a computer storage medium configured to store a computer program that, when executed on a computer, performs the following method:
  acquiring cervical blood flow data from an ultrasound data collecting device;
  determining cerebral perfusion data corresponding to the cervical blood flow data based on the cervical blood flow data and a mapping relationship between the cervical blood flow data and the cerebral perfusion data; and
  classifying cerebral perfusion states of a plurality of brain regions based on blood perfusion characteristics of the plurality of brain regions in the cerebral perfusion data.

In a fifth aspect, embodiments of the present application provide a cerebral perfusion state classification method, which includes:

acquiring cervical blood flow data from an ultrasound data collecting device;

determining sensitive brain regions corresponding to the cervical blood flow data based on the cervical blood flow data and a mapping relationship between the cervical blood flow data and the sensitive brain regions in a plurality of brain regions;

determining cerebral perfusion data corresponding to the cervical blood flow data in the sensitive brain regions based on the sensitive brain regions, the cervical blood flow data, and a mapping relationship between the cervical blood flow data and the cerebral perfusion data; and classifying cerebral perfusion states of the sensitive brain regions based on blood perfusion characteristics of the sensitive brain regions in the cerebral perfusion data.

In a sixth aspect, embodiments of the present application provide a method for training a cerebral perfusion state classification model, which includes:

acquiring cervical blood flow data from an ultrasound data collecting device;

acquiring cerebral perfusion data, wherein the cerebral perfusion data include qBOLD data and ASL data;

selecting sensitive brain regions that are the most relevant to changes in the cervical blood flow data from a plurality of brain regions according to a dynamic time warping distance between the cervical blood flow data and the qBOLD data; and calculating cerebral blood flow of the sensitive brain regions based on the ASL data, and classifying cerebral perfusion states of the sensitive brain regions according to the cerebral blood flow of the sensitive brain regions.

According to the solutions provided in the embodiments of the present application, the transceiving module acquires cervical blood flow data from an ultrasound data collecting device; and then, the processor determines cerebral perfusion data corresponding to the cervical blood flow data based on the cervical blood flow data and a mapping relationship between the cervical blood flow data and the cerebral perfusion data, and classifies cerebral perfusion states of a plurality of brain regions based on blood perfusion characteristics of the plurality of brain regions in the cerebral perfusion data.

According to the technical solutions of the present application, cervical blood flow data can be adopted to predict corresponding cerebral perfusion data, and then cerebral perfusion states of various brain regions can be more completely and accurately distinguished based on blood perfusion characteristics (e.g. cerebral blood flow) in the cerebral perfusion data, which greatly simplifies the acquisition of cerebral perfusion states, expands the application scenarios (e.g. aerospace scenarios and outdoor emergency scenarios) of brain examination, and can improve the accuracy of evaluation results of cerebral blood flow and cerebral functions, and assist doctors in completing brain examinations.

BRIEF DESCRIPTION OF THE DRAWINGS

In order to more clearly explain the technical solutions in the embodiments of the present application or the prior art, the drawings used in the description of the embodiments or the prior art will be briefly introduced below. Obviously, the drawings in the following description are some embodiments of the present application, and other drawings can further be obtained by those of ordinary skill in the art according to these drawings without involving any creative effort. In the figures.

DETAILED DESCRIPTION OF EXAMPLE EMBODIMENTS

Figure 1:
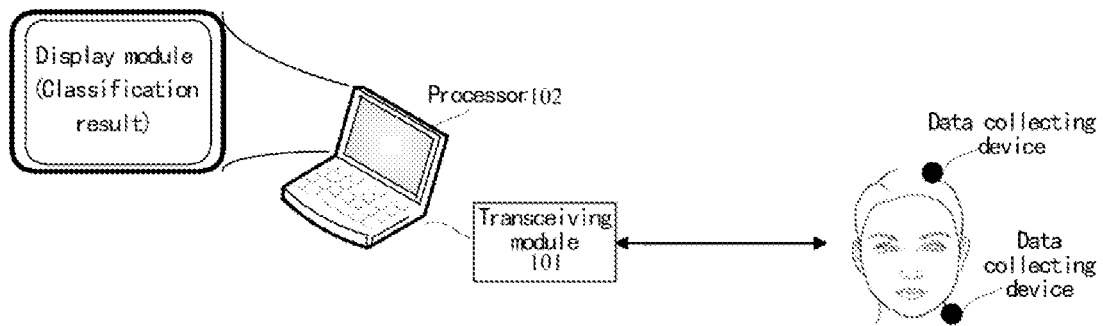
FIG. 1 is a schematic structural diagram of a cerebral perfusion state classification apparatus according to embodiments of the present application.

Before introducing the technical solutions provided in various embodiments of the present application, a brief description of the proper nouns involved here will be made.

In order to make the objectives, technical solutions, and advantages of the embodiments of the present application clearer, the technical solutions in the embodiments of the present application will be clearly and completely described below with reference to the drawings in the embodiments of the present application. Obviously, the described embodiments are only some but not all of the embodiments. All other embodiments obtained by those of ordinary skill in the art based on the embodiments in the present application without involving any creative effort shall fall within the scope of protection of the present application.

The terms used in the embodiments of the present application are only for the purpose of describing specific embodiments, and are not intended to limit the present application. The singular forms "a", "the", and "this" used in the embodiments of the present application and the appended claims are also intended to include plural forms. Unless otherwise specified, "a plurality of" generally means a condition of at least two, but does not exclude a condition of at least one.

It should be understood that the term "and/or" used here is only an association for describing associated objects, which means three relationships. For example, A and/or B, which means three conditions, that is, only A exists, A and B exist at the same time, and only B exists. In addition, the sign "/" here generally means an "or" relationship between before and after associated objects.

It should be understood that although the terms "first", "second", "third", etc. may be adopted in the embodiments of the present application to describe XXX, these XXX should not be limited to these terms. These terms are only used to distinguish XXX from each other. For example, under a condition without departing the scope of the embodiments of the present application, first XXX may be also known as second XXX, similarly, second XXX may also be known as first XXX. Depending on the context, the words "if" and "in case" used here may be interpreted as "at"

or "when" or "in response to determining" or "in response to monitoring". Similarly, depending on the context, the phrase "if it is determined that" or "if it is monitored that (stated condition or event)" may be interpreted as "when it is determined that" or "in response to determining" or "when it is monitored that (stated condition or event)" or "in response to monitoring (stated condition or event)".

It also should be noted that the terms "include", "comprise" or any other variation thereof are intended to cover non-exclusive inclusion such that a commodity or system including a series of elements includes not only those elements but also other elements not explicitly listed, or it further includes elements inherent to the commodity or system. Without further limitation, an element defined by the phrase "include a . . . " does not exclude the presence of additional same elements in the commodity or system that includes the element.

First, the implementation background of the present application will be described. At present, cerebral perfusion imaging is mainly used to reflect a blood perfusion state of a brain tissue. By the cerebral perfusion imaging, the actual condition of cerebral vessels can be restored as much as possible to assist in evaluating cerebral blood flow and a cerebral functional state.

In related technologies, large devices, such as computed tomography (CT) and magnetic resonance imaging (MRI), are often used for examination, and then, cerebral blood flow and a cerebral functional state are evaluated according to examination results.

However, the examination devices in related technologies are complicated to operate, and needed to be controlled by specialized technical personnel. Moreover, they are often bulky, and usually installed in fixed places such as hospitals. Therefore, it is difficult to apply the cerebral perfusion imaging to some special scenarios. For example, in aerospace scenarios, a cerebral perfusion state of a spaceman cannot be detected by using the large examination devices in the prior art due to gravity change in the space environment and limited space in a space capsule, causing impossibility of evaluation of cerebral blood flow and cerebral functions of the spaceman in the space environment. For another example, in outdoor emergency scenarios, an accident site is usually inaccessible (remote location or nearby congestion), and it is often difficult to transport the injured to a hospital with the examination devices in time. Therefore, emergency personnel are often unable to know a cerebral perfusion state of the injured in time, which affects the treatment of the injured.

Therefore, a technical solution capable of solving at least one of the above problems is to be proposed.

A subject for executing the technical solutions provided in the embodiments of the present application may be one apparatus or a plurality of apparatuses. The apparatus includes, but is not limited to, apparatuses integrated in any terminal device such as a smart phone, a tablet computer, a personal digital assistant (PDA), a smart TV, a laptop computer, a desktop computer, and a smart wearable device. The apparatus includes a transceiving module configured to receive data to be processed (e.g. cervical blood flow data described below), and a processor configured to process the data to be processed. The processor of the apparatus can be carried in the above terminal device. The processor of the apparatus and the transceiving module can be integrated in the same device, or respectively integrated in different devices, which is not limited in the embodiments of the present application. Optionally, the apparatus further includes a display module configured to display a processing result of the apparatus, such as a screen of the terminal device.

In practice, the transceiving module of the apparatus can be connected to an examination apparatus integrated with an ultrasonic sensor, and the examination apparatus is arranged at a target evaluation object end. The examination apparatus, for example, is implemented as a neck examination apparatus integrated with an ultrasonic sensor, and the neck examination apparatus is connected to the apparatus integrated with the transceiving module. Of course, in order to adapt to a plurality of application scenarios, the neck examination apparatus may be connected to the apparatus integrated with the processor in a wire manner or a wireless manner such as WiFi, 5G, 4G, and Bluetooth.

In another embodiment, the transceiving module and the processor can be integrated in the same device. For example, the transceiving module and the processor can be integrated in a data analysis apparatus that is connected to the neck examination apparatus. Then, after acquiring data to be processed from the neck examination apparatus, the data analysis apparatus analyzes the data to be processed and displays a processing result, for example, by sending out a voice message for early warning, or displaying a classification result of cerebral perfusion states of various brain regions. Or, the neck examination apparatus transmits data to be processed to a terminal device with a function of analyzing data to be processed, and the terminal device displays a processing result.

In practice, hardware structures of the apparatus can be arranged according to specific application scenarios, and the embodiments of the present application are only exemplary, and are not intended to be a limitation.

It should be noted that no matter what kind of hardware structure the executive subject is implemented as, the core purpose of the executive subject is to acquire matching cerebral perfusion data based on cervical blood flow data, so that cerebral perfusion data can be obtained without using the large examination devices. Then, cerebral perfusion states of various brain regions are classified based on blood perfusion characteristics (e.g. cerebral blood flow) in the cerebral perfusion data, which greatly simplifies the acquisition of cerebral perfusion states, expands the application scenarios (e.g. aerospace scenarios and outdoor emergency scenarios) of brain examination, and can improve the accuracy of evaluation results of cerebral blood flow and cerebral functions, and assist doctors in completing brain examinations.

Specific implementation modes of the technical solutions will be described with reference to specific embodiments.

FIG. 1 is a schematic structural diagram of a cerebral perfusion state classification apparatus according to embodiments of the present application. As shown in FIG. 1, the apparatus includes the following modules:
   a transceiving module 101, configured to acquire cervical blood flow data from an ultrasound data collecting device; and
   a processor 102, configured to determine cerebral perfusion data corresponding to the cervical blood flow data based on the cervical blood flow data and a mapping relationship between the cervical blood flow data and the cerebral perfusion data; and
   further configured to classify cerebral perfusion states of a plurality of brain regions based on blood perfusion characteristics of the plurality of brain regions in the cerebral perfusion data.

Further, the apparatus may further include a display module configured to output a processing result of the processor 102, such as cerebral perfusion data, and a classification result of cerebral perfusion states of a plurality of brain regions.

It can be understood that the transceiving module 101 and the processor 102 can be located on the same device, or the transceiving module 101 is located locally, and the processor 102 is located on a remote server. Of course, the two structures described here are only exemplary, and in practice, hardware structures for integrating the transceiving module 101 and the processor 102 can be selected according to specific application scenarios.

First, the transceiving module 101 is configured to receive cervical blood flow data from an ultrasound data collecting device. The blood flowing through the brain must be transported via the neck. Therefore, the acquired cervical blood flow data can reflect cerebral blood flow to a certain extent, which facilitates the subsequent establishment of a mapping relationship between cervical blood flow and cerebral perfusion data and thus provides a basis for predicting cerebral perfusion data.

Specifically, the cervical blood flow data include, but are not limited to, any one or a combination of cervical vessel blood flow data and vascular lumen morphology change data. Optionally, the cervical blood flow data are continuous periodic data, such as a plurality of cervical blood flow data acquired by the ultrasound data collecting device based on a preset period.

For example, the ultrasound data collecting device continuously acquires a plurality of sets of cervical blood flow data according to the preset period. Each set of cervical blood flow data includes 5,156 cervical blood flow signals, and a corresponding 1×5156 matrix is formed by these signals.

In practice, the transceiving module 101 can be connected to an ultrasound data collecting device integrated with an ultrasonic probe. For example, the ultrasound data collecting device can be implemented based on intravenous ultrasound (IVUS).

In the embodiments of the present application, the processor 102 refers to a local device for identifying and processing acquired cervical blood flow data. The processor 102 may be a local processor, or a remote server or server cluster, or a virtual processor in a cloud server.

After receiving the cervical blood flow data from the transceiving module 101, the processor 102 needs to use the cervical blood flow data to predict cerebral perfusion data. In practice, the cerebral perfusion data are image data obtained by cerebral perfusion imaging.

For example, the cerebral perfusion data may be an ASL magnetic resonance image sequence obtained by arterial spin labeling (ASL). ASL is a cerebral perfusion imaging method without using a contrast agent, and can reflect blood perfusion information of a brain tissue from different perspectives. According to ASL, usually endogenous protons in the blood are usually labeled with a saturation pulse or an inversion sequence at the upstream of the region of interest, and signals are acquired in the region of interest.

ASL has natural repeatability, and can be used to repeatedly observe changes in blood perfusion within a relatively short period. Therefore, optionally, ASL is adopted to obtain a plurality of sets of ASL sequences serving as cerebral perfusion data samples for training a network model below.

In order to further improve the accuracy of prediction results, in the present application, further optionally, the brain is divided into 116 brain regions (including 90 cerebrum regions and 26 cerebellum regions) according to an AAL template. Based on the divided 116 brain regions, average values (e.g. average ASL time sequences) of cerebral perfusion data samples (e.g. ASL data) corresponding to various brain regions are calculated, and then, a corresponding 1×116 matrix is constructed based on the average values of the cerebral perfusion data samples in the 116 brain regions. The division of the brain here is only exemplary, and is not intended to be a limitation. This facilitates subsequent mapping of the cerebral perfusion data in various brain regions, thereby further improving the accuracy of a prediction result of the cerebral perfusion data.

For another example, the cerebral perfusion data may also be a CT image or an MRI image. In practice, the CT image and the MRI image can be obtained in advance by the relevant techniques, and specific acquisition methods will not be limited here. Similarly, the CT image and the MRI image can be divided according to the above division method, which will not be described in detail here.

Specifically, in a possible embodiment, the processor 102 determines cerebral perfusion data corresponding to the acquired cervical blood flow data based on the cervical blood flow data acquired by the transceiving module 101 and a mapping relationship between the cervical blood flow data and the cerebral perfusion data.

The cerebral perfusion data include cerebral perfusion data of a plurality of brain regions. Optionally, the cerebral perfusion data of the plurality of brain regions can be displayed based on the cerebral perfusion data, or a classification result that will be described below is output. For example, an output result shows that a brain region A belongs to a cerebral perfusion state type 1, a brain region B belongs to a cerebral perfusion state type 2, etc.

Optionally, when determining cerebral perfusion data corresponding to the acquired cervical blood flow data based on the cervical blood flow data acquired by the transceiving module 101 and a mapping relationship between the cervical blood flow data and the cerebral perfusion data, the processor 102 is specifically configured to:

extract cervical blood flow characteristics from the cervical blood flow data; and input the cervical blood flow characteristics into a pre-trained network model to obtain cerebral perfusion data corresponding to the cervical blood flow characteristics.

In the embodiments of the present application, the network model is trained based on cervical blood flow characteristic samples and cerebral perfusion data samples. Optionally, the network model includes, but is not limited to, a Seq2Seq model including an encoder and a decoder. The Seq2Seq model is a deep learning model constructed based on long short-term memory (LSTM). The Seq2Seq model includes an encoder and a decoder that are constructed based on LSTM.

In addition, the network model can also be implemented as a model constructed based on a gate recurrent unit (GRU), or a deep learning model constructed based on Transformer.

For example, at the above steps, it is hypothesized that the cerebral perfusion data is an ASL sequence. It is hypothesized that the pre-trained network model is a Seq2Seq model. It is hypothesized that the cervical blood flow data are a cervical blood flow sequence.

Based on the above hypotheses, the cervical blood flow sequence is converted by the encoder into a cervical blood flow characteristic vector. The length of the cervical blood flow characteristic vector may be fixed. Then, the cervical blood flow characteristic vector is input into the decoder of the Seq2Seq model to obtain an ASL sequence (i.e. cerebral perfusion prediction data) corresponding to the cervical blood flow characteristic vector.

Figure 2:
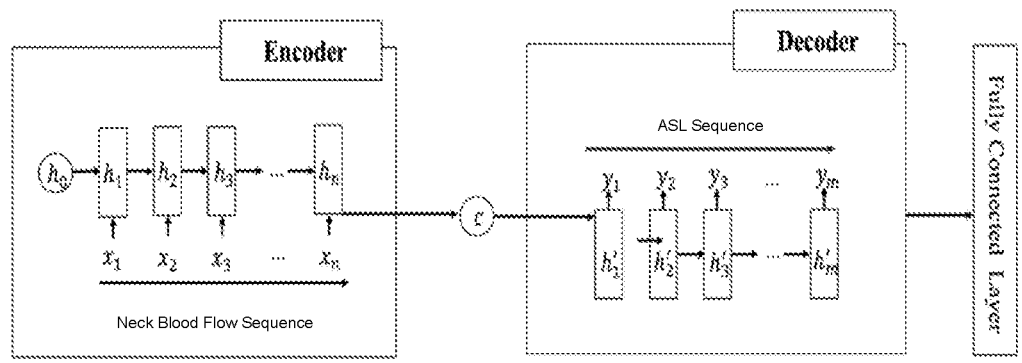
FIG. 2 and FIG. 3 are schematic diagrams of a cerebral perfusion state classification apparatus according to embodiments of the present application.

In an optional embodiment, the encoder and the decoder of the Seq2Seq model described above are shown in FIG. 2. In FIG. 2, $X=\{x_1, x_2, \ldots x_n\}$ represents a cervical blood flow sequence with a length of n, and $Y=\{y_1, y_2, \ldots y_m\}$ represents an ASL sequence with a length of m. $\{h_1, h_2, \ldots, h_m\}$ is a hidden layer state, and c is a cervical blood flow characteristic vector converted from the cervical blood flow sequence by the encoder. Optionally, the ASL sequence output by the decoder is input into a fully connected layer.

Optionally, a mean square error (MSE) is used as a loss function of the above Seq2Seq model. A difference between the cervical blood flow sequence and the ASL sequence can be reduced continuously by back propagation of the Seq2Seq model. The loss function converges quickly, so it has great advantages in practical applications. A formula of the loss function is as follows:

$$MSE = \frac{\sum_{i=1}^{n}(y_i - y_i^p)^2}{n}$$ Formula 1

Figure 3:
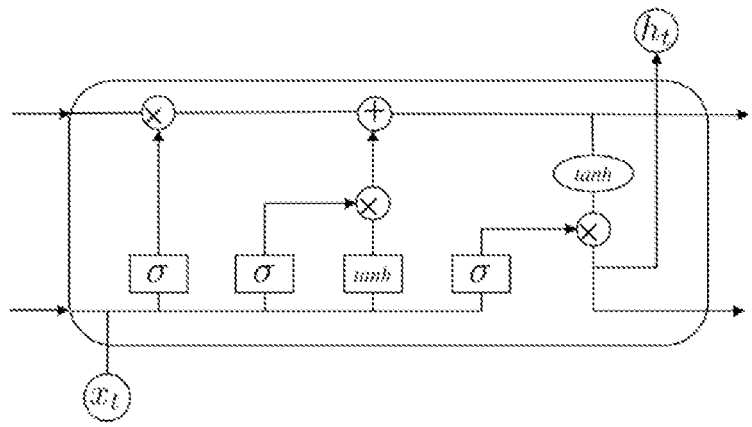

In the deep learning model constructed based on LSTM, specifically, a more accurate prediction result can be obtained by adding intermediate cell state information for back propagation. In an optional embodiment, as shown in FIG. 3, three control switches, that is, a forget gate, an input gate, and an output gate, are added into a deep learning model (e.g. Seq2Seq model).

Specifically, in the deep learning model, the forget gate $f_t$ is obtained from current input $x_t$ and previous output $h_{t-1}$, and $f_t$ determines what to discard from a previous cell state $C_{t-1}$. Each value in $f_t$ is a numerical value from 0 to 1, with 1 representing fully reservation and 0 representing complete deletion. The forget gate $f_t$ is specifically realized as follows:

$f_t = \sigma(w_f \cdot h_{t-1} + u_f \cdot x_t + b_f)$ Formula 2

The input gate $i_t$ is configured to update important information. For example, $i_t$ is obtained from current input $x_t$ and previous output $h_{t-1}$, and $i_t$ is configured to determine new information that needs to be added into the current cell state $C_t$. Here, the new information is expressed by $\tilde{C}_t$. The input gate $i_t$ is specifically realized as follows:

$i_t = \sigma(w_i \cdot h_{t-1} + u_i \cdot x_t + b_i)$ Formula 3

$\tilde{c}_t = \tan h(w_c \cdot h_{t-1} + u_c \cdot x_t + b_c)$ Formula 4

$c_t = f_t \odot c_{t-1} + i_t \odot \tilde{C}_t$ Formula 5

The output gate $o_t$ is configured to determine an output value of the model. $o_t$ determines how much information to output into $h_t$. The output gate $o_t$ is specifically realized as follows:

$o_t = \sigma(w_o \cdot h_{t-1} + u_o \cdot x_t + b_o)$ Formula 6

$h_t = o_t \tan h \odot(C_t)$ Formula 7

Of course, in addition to the Seq2Seq model described above, other deep learning models or other neural networks can also be used to realize the prediction function of the processor 102 described above, which is not limited in the present application.

After the network models that may be used in the present application are introduced, a method for acquiring training data for training the above network models will be described below, such as cervical blood flow characteristic samples and cerebral perfusion data samples that are used for training a network model.

First, cervical blood flow data of a target examination object can be acquired by using an ultrasound data collecting device. Optionally, the cervical blood flow data are converted into a cervical blood flow characteristic matrix, and the number of elements in the matrix is determined by the quantity of the cervical blood flow data.

Then, cerebral perfusion data being an ASL sequence are taken as an example, and a method for acquiring the cerebral perfusion data described above specifically includes the following steps:

a brain magnetic resonance image obtained based on ASL is received; a plurality of brain regions are divided in the brain magnetic resonance image; and cerebral perfusion data of each of the plurality of brain regions are used as a cerebral perfusion data sample.

Specifically, in practice, a brain magnetic resonance image of the same target examination object is acquired by using a device with an ASL acquisition function. Then, the brain magnetic resonance image obtained based on ASL is received, the brain magnetic resonance image is divided into brain magnetic resonance images corresponding to a plurality of brain regions according to a preset manner, and then an ASL time sequence of each of the plurality of brain regions is generated. Finally, an average ASL time sequence of the plurality of brain regions is used as a cerebral perfusion data sample for training the network model. Optionally, the average ASL time sequence is converted into an ASL characteristic matrix, and the number of elements in the matrix is determined by the quantity of brain regions.

Optionally, the cerebral perfusion data samples are labeled with corresponding classification labels, and then the cerebral perfusion data samples carrying the classification labels are used in the training process of a cerebral perfusion state classification model described below.

In the prior art, the classification of cerebral perfusion states of brain regions usually depends on the experience and observation of relevant technical personnel, so that the accuracy of classification results is difficult to guarantee.

After predicting cerebral perfusion data matching the cervical blood flow data, the processor 102 is further configured to classify cerebral perfusion states of a plurality of brain regions based on blood perfusion characteristics of the plurality of brain regions in the cerebral perfusion data.

Optionally, when classifying cerebral perfusion states of a plurality of brain regions based on blood perfusion characteristics of the plurality of brain regions in the cerebral perfusion data, the processor 102 is specifically configured to:

extract blood perfusion characteristics of a plurality of brain regions from the cerebral perfusion data; and determine a cerebral perfusion state type to which each of the plurality of brain regions belongs according to the blood perfusion characteristics and blood perfusion characteristic thresholds corresponding to cerebral perfusion state types.

In practice, the blood perfusion characteristics thresholds are set to be one or more numerical ranges. The numerical range includes a hypoperfusion threshold. For example, the hypoperfusion threshold can be set to be 20 mL·100 g−1·min−1. In short, various cerebral perfusion state types have corresponding blood perfusion characteristic threshold ranges, and end points of the ranges are hyperperfusion thresholds and hypoperfusion thresholds, respectively. If a blood perfusion characteristic value of a certain brain region is greater than a hyperperfusion threshold of a certain type, or the blood perfusion characteristic value is less than a hypoperfusion threshold of the type, then it is determined that a cerebral perfusion state of the brain region does not belong to the type.

For example, it is hypothesized that the blood perfusion characteristics include cerebral blood flow (CBF), and it is hypothesized that the blood perfusion characteristic threshold is a cerebral blood flow threshold.

Based on the above hypotheses, at the above steps, cerebral blood flow of each of the plurality of brain regions is calculated based on the cerebral perfusion data. Optionally, the calculated cerebral blood flow of each of the plurality of brain regions can be directly displayed. For example, a result shows that blood flow of a brain region a is XX, and blood flow of a brain region b is YY.

Then, it is hypothesized a cerebral blood flow threshold is set for each of the plurality of brain regions. It is hypothesized that the cerebral perfusion state types of various brain regions include a type I and a type II.

Based on the above hypothesis, for the cerebral blood flow of each of the plurality of brain regions, it is determined that the cerebral blood flow of each of the plurality of brain regions satisfies a cerebral blood flow threshold of a specific type set in the region. If the cerebral blood flow satisfies a cerebral blood flow threshold of the type I set in the region, then it is determined that a cerebral perfusion state of the brain region belongs to the type I. If the cerebral blood flow satisfies a cerebral blood flow threshold of the type II set in the region, then it is determined that the cerebral perfusion state of the brain region belongs to the type II. In practice, the type I represents normal cerebral blood flow, and the type II represents abnormal cerebral blood flow. For example, if it is determined that a brain region a belongs to the type I, then a result of "brain region a, cerebral blood flow is normal" is displayed; and if it is determined that a brain region b belongs to the type II, then a result of "brain region b, cerebral blood flow is abnormal" is displayed, thereby assisting doctors in completing brain examination evaluation by the display content.

Of course, in addition to the type I and the type II, cerebral perfusion state types of various brain regions can also be set to be three or more types. For example, the types include normal cerebral blood flow, slightly high cerebral blood flow, moderately high cerebral blood flow, high cerebral blood flow, slightly low cerebral blood flow, moderately low cerebral blood flow, and low cerebral blood flow. The high and low levels described here are actually determined according to a numerical range of cerebral blood flow thresholds.

Optionally, if the blood perfusion characteristics include cerebral blood flow, then the processor 102 is also configured to set cerebral blood flow thresholds corresponding to cerebral perfusion state types. Each target examination object has individual characteristic information. Therefore, optionally, cerebral blood flow thresholds are dynamically configured according to gender, age, weight, and other individual characteristic information to further improve the accuracy of classification results. For example, different cerebral blood flow threshold ranges are set for men and women, respectively.

The above cerebral perfusion state classification apparatus provided in the present application can adopt cervical blood flow data to predict corresponding cerebral perfusion data, and then more completely and accurately distinguish cerebral perfusion states of various brain regions based on blood perfusion characteristics (e.g. cerebral blood flow) in the cerebral perfusion data, which greatly simplifies the acquisition of cerebral perfusion states, expands the application scenarios (e.g. aerospace scenarios and outdoor emergency scenarios) of brain examination, and can improve the accuracy of evaluation results of cerebral blood flow and cerebral functions, and assist doctors in completing brain examinations.

In the above and below embodiments, optionally, the processor 102 is further configured to label sensitive brain regions, and set corresponding blood perfusion characteristic thresholds for the sensitive brain regions so as to improve the efficiency of cerebral perfusion classification. By classifying cerebral perfusion states of the sensitive brain regions, a cerebral perfusion state of a brain region that needs to be observed can be indicated, which further improves the efficiency of brain examination evaluation.

Specifically, in a possible embodiment, the processor 102 is further specifically configured to determine sensitive brain regions corresponding to cervical blood flow data based on the cervical blood flow data and a mapping relationship between the cervical blood flow data and the sensitive brain regions in a plurality of brain regions.

The mapping relationship between the cervical blood flow data and the sensitive brain regions of the plurality of brain regions can be constructed as a network model, or can be constructed as a data mapping table, or can be constructed in other forms. For example, it is hypothesized that a network model b constructed based on a mapping relationship between cervical blood flow data and sensitive brain regions in a plurality of brain regions is arranged in advance, based on this, the cervical blood flow data can be converted into a cervical blood flow characteristic sequence, which is input into the network model b to obtain a sensitive brain region corresponding to the cervical blood flow characteristic sequence output by the network model b.

For another example, it is hypothesized that a data mapping table a is stored in a server. It is hypothesized that a mapping relationship between cervical blood flow data and sensitive brain regions in a plurality of brain regions is stored in the data mapping table a. Based on this, the processor 102 can extract cervical blood flow characteristics, such as cervical blood flow, from the acquired cervical blood flow data, and then search for a corresponding sensitive brain region from the data mapping table a based on the cervical blood flow characteristics.

Of course, in addition to the above examples, there are many methods for screening sensitive brain regions, which will not described in detail here. Regardless of the methods of screening sensitive brain regions, the core is: to create a mapping relationship between cervical blood flow data and sensitive brain regions in a plurality of brain regions, and then, and screen out a sensitive brain region corresponding to current cervical blood flow data based on the mapping relationship.

How to create a mapping relationship between cervical blood flow data and sensitive brain regions in a plurality of brain regions will be described below with reference to specific examples.

In the present application, the sensitive brain region refers to a region affected by brain evaluation indexes. In short, the sensitive brain region refers to a region related to changes in brain evaluation indexes. It is easy to understand that the sensitive brain region includes, but is not limited to, a brain region that needs special attention, or a brain region with key functions, or a brain region that is easily ignored but has diagnostic significance, etc. The brain evaluation indexes include various cervical blood flow indexes such as the blood oxygen level, blood flow, and vascular occlusion. A method for screening sensitive brain regions will be described below by taking the blood oxygen level as an example.

The cerebral perfusion data include quantitative blood oxygen level dependent (qBOLD) data. The qBOLD data are mainly used to reflect the blood oxygen level of the brain (of an examination object). Specifically, qBOLD can be used to effectively reflect functional changes such as cerebral blood flow and metabolic activity of an examination object in various states (e.g. a resting state and a loading state) by measuring changes in blood flow and blood oxygenation levels, and is an effective manner for studying anomalous cerebral function connection. Optionally, qBOLD signals are separated from venous blood oxygenation (Yv) and deoxygenated blood volume (DBV) so as to obtain qBOLD data.

In practice, the qBOLD data can provide measured values of local and absolute in vivo blood oxygen saturation, and the activity level of neurocytes in various brain regions can be reflected according to changes in local signals to achieve the purpose of studying brain activities in a non-invasive manner.

In order to further improve the accuracy of prediction results, in the present application, further optionally, the brain is divided into 116 brain regions (including 90 cerebrum regions and 26 cerebellum regions) according to an AAL template. Then, the accuracy of prediction is further improved by taking the divided brain regions as the basis for analysis. In practice, according to qBOLD, a plurality of sets of qBOLD data will be acquired within a plurality of continuous time points. For example, for the same subject, 200 sample data are acquired, then, average values of brain magnetic resonance samples (e.g. qBOLD data) corresponding to various brain regions of the subject are calculated based on the divided 116 brain regions, and a corresponding 200×116 qBOLD average time sequence sample matrix is constructed based on the average values of the brain magnetic resonance samples in the 116 brain regions of the subject. The above division of brain regions is only exemplary, and in practice, brain regions can be divided by adopting other templates, which is not limited here. This facilitates subsequent mapping of the cerebral perfusion data in various brain regions, thereby further improving the accuracy of a prediction result of the cerebral perfusion data.

Further, based on the above hypotheses, sample data with relatively high noise can further be filtered from the 200 sample data, 190 sample data are remained, and then, a corresponding 190×116 qBOLD average time sequence sample matrix is constructed based on the above method. Thus, the quality of samples can be further improved, and a training effect is improved.

After the cerebral perfusion data are introduced, how to create a mapping relationship between cervical blood flow data and sensitive brain regions in a plurality of brain regions will be described below with reference to specific examples.

Specifically, in an optional embodiment, when creating a mapping relationship between cervical blood flow data and sensitive brain regions in a plurality of brain regions, the processor 102 is further configured to:

select sensitive brain regions that are the most relevant to changes in the cervical blood flow data from a plurality of brain regions according to a dynamic time warping (DTW) distance, and construct a mapping relationship between the cervical blood flow data and the sensitive brain regions.

The DTW algorithm is a method for aligning sequences on the time axis. In practice, the principle of creating a mapping relationship between cervical blood flow data and sensitive brain regions based on the DTW algorithm is specifically as follows.

It is hypothesized that a qBOLD sequence is X, the length is n, that is, $X=\{x_1, x_2, \ldots x_n\}$. It is hypothesized that a cervical blood flow data sequence is Y, the length is m, that is, $Y=\{y_1, y_2, \ldots y_m\}$. Based on the above hypotheses, a n×m dimension matrix can be constructed according to the two data sequences, then a DTW distance between any two points on the two data sequences is:

$$\gamma(i,j)=\{[d(x_i,y_i)]^2\{\min[\gamma(i-1,j-1),\gamma(i-1,j), \gamma(i,j-1)]\}^2\}^{1/2}$$

where, $d(x_i, y_i)$ is a distance between two data sequence points $x_i$ and $y_i$; and $\gamma(i,j)$ is the minimum accumulative distance from an element $(x_1, y_1)$ to an element $(x_i, y_i)$. i is less than n, and i is less than m.

Specifically, a function for measuring similarity between sequences X and Y can be represented by a DTW distance:

$$\frac{1}{SIM(X,Y)} = DTW(X,Y) = \gamma(i,j)$$

The DTW algorithm has warping properties, and can achieve comparison of local characteristics of two sequences by well-timed conversion, expansion, and compression. Furthermore, there is no requirement for lengths of sequences involving in comparison. During comparison, distances between one point on one sequence and a plurality of points on the other sequence may be compared, or some points will be ignored directly during comparison of distances. Therefore, the DTW algorithm can be used to compare similarity between sequences with different lengths, and has relatively good robustness against disturbances of the time axis.

qBOLD data are taken as an example, a mapping relationship between qBOLD and cervical blood flow data that are not equal in the length can be effectively constructed based on a dynamic time warping distance between the cervical blood flow data and the qBOLD data.

At the above steps, it is hypothesized that the cervical blood flow data include a cervical blood flow characteristic sequence. It is hypothesized the qBOLD data include a qBOLD average time sequence of each of a plurality of brain region. Based on this, an optional implementation method for selecting sensitive brain regions that are the most relevant to changes in cervical blood flow data from a plurality of brain regions, specifically includes:

dynamic time warping distance sequences of various qBOLD average time sequences and the cervical blood flow characteristic sequence are calculated; peak values and/or trough values in the dynamic time warping distance sequences corresponding to various qBOLD average time sequences are determined; and brain regions corresponding to the peak values and/or trough values are used as sensitive brain regions.

At the above steps, brain regions that are the most relevant to changes in the cervical blood flow data can be obtained by screening the peak values and/or trough values from the dynamic time warping distance sequences of the qBOLD average time sequence of each of the plurality of brain regions and the cervical blood flow characteristic sequence. Here, the brain regions corresponding to the peak values and trough values can be regarded as brain regions that are significantly affected by changes in cervical blood flow, i.e. the sensitive brain regions described above.

In another embodiment, it is hypothesized the cervical blood flow data include first cervical blood flow data in a first state, and second cervical blood flow data in a second state. It is hypothesized that qBOLD data of any brain region in the plurality of brain regions include first qBOLD data of the brain region in the first state, and second qBOLD data of the brain region in the second state.

Based on the above hypotheses, for any brain region, when creating a mapping relationship between cervical blood flow data and sensitive brain regions in a plurality of brain regions, the processor is further configured to:

acquire a cervical blood flow difference sample of the first cervical blood flow data and the second cervical blood flow data; acquire a qBOLD difference sample of the first qBOLD data and the second qBOLD data; calculate a dynamic time warping distance sequence of the cervical blood flow difference sample and the qBOLD difference sample; take brain regions corresponding to peak values and/or trough values in the dynamic time warping distance sequence of the cervical blood flow difference sample and the qBLOD difference sample as sensitive brain regions, and construct a mapping relationship between the cervical blood flow data and the sensitive brain regions.

According to the above steps, change trends of cerebral perfusion data when switching between different states are compared, and sensitive brain regions that are easily affected by changes in blood oxygen levels are screened out based on a comparison result, so that subsequent analysis can be made based on the sensitive brain regions, which improves the pertinence of subsequent analysis and further improves the accuracy of prediction of cerebral perfusion data.

In practice, the first state may be a resting state, and the second state may be a loading state. Of course, the above states can be dynamically set. For example, the loading state may also be divided into a plurality of sub-states, such as aerobic loading and anaerobic loading.

In practice, there may be some differences in sensitive brain regions of different people. For example, there are differences between children and elder people, between manual workers and mental workers, and between men and women. In order to avoid missing some brain regions that need to be analyzed selectively, in another embodiment, a mapping relationship between cervical blood flow data, individual differentiated characteristics, and sensitive brain regions based on the individual differentiated characteristics (e.g. age, gender, health condition, exercise condition, living environment, and career). Then, sensitive brain regions are screened based on the mapping relationship. Of course, the individual differentiated characteristics described here are only exemplary, which are not limited here.

In summary, through the above processing procedure provided in the present embodiment, the processor 102 can acquire corresponding sensitive brain regions based on cervical blood flow data.

Figure 4:
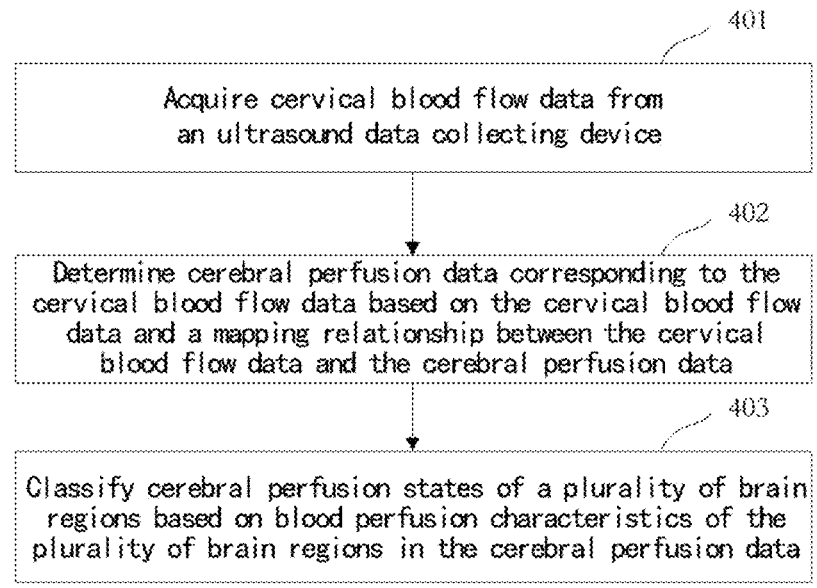
FIG. 4 is a schematic flowchart of a cerebral perfusion state classification method according to embodiments of the present application.

FIG. 4 is schematic flowchart of a cerebral perfusion state classification method according to embodiments of the present application, which specifically includes the following steps.

At step 401, cervical blood flow data are acquired from an ultrasound data collecting device.

At step 402, cerebral perfusion data corresponding to the cervical blood flow data are determined based on the cervical blood flow data and a mapping relationship between the cervical blood flow data and the cerebral perfusion data.

At step 403, cerebral perfusion states of a plurality of brain regions are classified based on blood perfusion characteristics of the plurality of brain regions in the cerebral perfusion data.

Optionally, the step, at which cerebral perfusion data corresponding to the cervical blood flow data are determined based on the cervical blood flow data and a mapping relationship between the cervical blood flow data and the cerebral perfusion data, includes:

cervical blood flow characteristics are extracted from the cervical blood flow data; and the cervical blood flow characteristics are input into a pre-trained network model to obtain cerebral perfusion data corresponding to the cervical blood flow characteristics.

The network model is trained based on cervical blood flow characteristic samples and cerebral perfusion data samples.

Optionally, the method further includes:

a brain magnetic resonance image obtained based on arterial spin labeling is received;

a plurality of brain regions are divided in the brain magnetic resonance image; and cerebral perfusion data of each of the plurality of brain regions are used as the cerebral perfusion data sample.

Optionally, the network model includes a Seq2Seq model including an encoder and a decoder; and the Seq2Seq model includes an encoder and a decoder that are constructed based on long short-term memory (LSTM).

Optionally, the step, at which cerebral perfusion states of a plurality of brain regions are classified based on blood perfusion characteristics of the plurality of brain regions in the cerebral perfusion data, includes:

blood perfusion characteristics of a plurality of brain regions are extracted from the cerebral perfusion data; and a cerebral perfusion state type to which each of the plurality of brain regions belongs is determined according to the blood perfusion characteristics and blood perfusion characteristic thresholds corresponding to cerebral perfusion state types.

Optionally, the blood perfusion characteristics include cerebral blood flow.

The method further includes: cerebral blood flow thresholds corresponding to cerebral perfusion state types are set.

Optionally, the cervical blood flow data include one or a combination of cervical vessel blood flow data and vascular lumen morphology change data.

It is worthwhile to note that the cerebral perfusion state classification method is similar to the implementation modes of the cerebral perfusion state classification apparatus provided in FIG. 1, and the similarities refer to the above, and will not be described in detail here.

Figure 5:
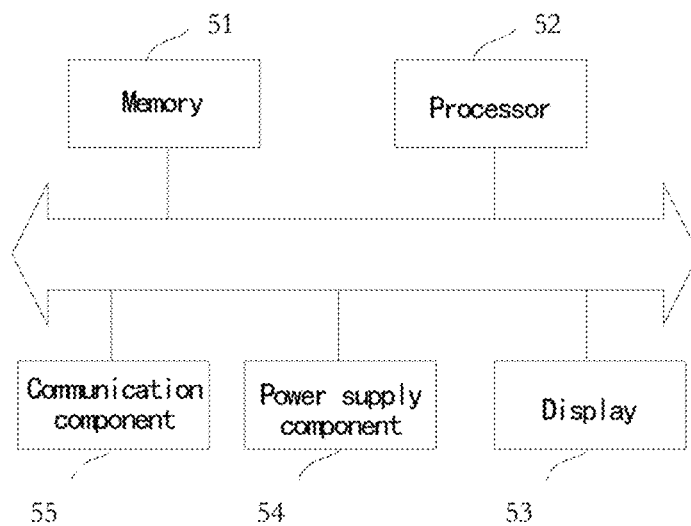
FIG. 5 is a schematic structural diagram of an electronic device according to embodiments of the present application.

FIG. 5 is a schematic structural diagram of an electronic device according to embodiments of the present application. As shown in FIG. 5, the electronic device includes: a memory 51 and a processor 52, wherein the memory 51 is configured to store a program; and the processor 52 is coupled with the memory and configured to execute the program stored in the memory so as to:

acquire cervical blood flow data from an ultrasound data collecting device;

determine cerebral perfusion data corresponding to the cervical blood flow data based on the cervical blood flow data and a mapping relationship between the cervical blood flow data and the cerebral perfusion data; and classify cerebral perfusion states of a plurality of brain regions based on blood perfusion characteristics of the plurality of brain regions in the cerebral perfusion data.

The above memory 51 can be configured to store other data so as to support operations on a computer device. Examples of these data include any application program or instructions of methods that are operated on the computer device. The memory 51 can be implemented by any type of volatile or non-volatile storage device or a combination thereof, such as a static random access memory (SRAM), an electrically erasable programmable read-only memory (EEPROM), an erasable programmable read-only memory (EPROM), a programmable read only memory (PROM), a read-only memory (ROM), a magnetic storage, a flash memory, a magnetic disk, and an optical disk.

When executing the program in the memory 51, the processor 52 can also realize functions in addition to the above functions, which can specifically refer to the description of the foregoing embodiments.

Further, as shown in FIG. 5, the electronic device further includes other components such as a display 53, a power supply component 54, and a communication component 55. Some components are schematically shown in FIG. 5, and the electronic device may include other components in addition to the components shown in FIG. 5.

In addition to the above embodiments, in an optional embodiment, the cerebral perfusion state classification apparatus provided in FIG. 1 can also be implemented in other manners. As shown in FIG. 1, the apparatus includes the following modules:

a transceiving module 101, configured to acquire cervical blood flow data from an ultrasound data collecting device; and a processor 102, configured to determine sensitive brain regions corresponding to the cervical blood flow data based on the cervical blood flow data and a mapping relationship between the cervical blood flow data and the sensitive brain regions in a plurality of brain regions; and also configured to determine cerebral perfusion data corresponding to the cervical blood flow data in the sensitive brain regions based on the sensitive brain regions, the cervical blood flow data, and a mapping relationship between the cervical blood flow data and the cerebral perfusion data; and classify cerebral perfusion states of the plurality of brain regions based on the cerebral perfusion data.

Optionally, the transceiving module 101 is further configured to receive cerebral perfusion data from a cerebral perfusion data acquisition device, and the cerebral perfusion data include quantitative blood oxygen level dependent (qBOLD) data.

When creating a mapping relationship between cervical blood flow data and sensitive brain regions in a plurality of brain regions, the processor 102 is further configured to select sensitive brain regions that are the most relevant to changes in cervical blood flow data from a plurality of brain regions according to a dynamic time warping distance between the cervical blood flow data and the qBOLD data, and construct a mapping relationship between the cervical blood flow data and the sensitive brain regions.

Optionally, the cervical blood flow data include a cervical blood flow characteristic sequence, and the qBOLD data include a qBOLD average time sequence of each of the plurality of brain regions. When selecting sensitive brain regions that are the most relevant to changes in cervical blood flow data from a plurality of brain regions according to a dynamic time warping distance between the cervical blood flow data and the qBOLD data, the processor 102 is specifically configured to:

calculate dynamic time warping distance sequences of various qBOLD average time sequences and the cervical blood flow characteristic sequence; determine peak values and/or trough values in the dynamic time warping distance sequences corresponding to various qBOLD average time sequences; and take brain regions corresponding to the peak values and/or trough values as sensitive brain regions.

Optionally, when generating a qBOLD average time sequence of each of the plurality of brain regions, the processor 102 is further configured to:

determine a plurality of brain regions according to a preset template; acquire qBOLD data from a brain magnetic resonance image; perform voxel mean processing on the qBOLD data according to the plurality of brain regions to obtain qBOLD data of each of the plurality of brain regions; and generate a qBOLD average time sequence sample of each of the plurality of brain regions based on the qBOLD data of each of the plurality of brain regions.

Optionally, when determining cerebral perfusion data corresponding to the cervical blood flow data in the sensitive brain regions based on the sensitive brain regions, the cervical blood flow data, and a mapping relationship between the cervical blood flow data and the cerebral perfusion data, the processor 102 is specifically configured to:

input the cervical blood flow data into a preset network model to obtain ASL data corresponding to the cervical blood flow data; and select ASL data corresponding to the sensitive brain regions from the ASL data corresponding to the cervical blood flow data. The network model is constructed based on the cervical blood flow data and the ASL data.

Optionally, the transceiving module 101 is further configured to receive cerebral perfusion data from a cerebral perfusion data acquisition device, and the cerebral perfusion data further include ASL average time sequences for training a network model.

When generating ASL average time sequences, the processor 102 is further configured to: determine a plurality of brain regions according a preset template; acquire ASL data from a brain magnetic resonance image; and perform voxel mean processing on the ASL data according to the plurality of brain regions to obtain an ASL average time sequence of each of the plurality of brain regions.

Optionally, when classifying cerebral perfusion states of the plurality of brain regions based on the cerebral perfusion data, the processor 102 is specifically configured to:

acquire blood perfusion characteristics of the sensitive brain regions from the cerebral perfusion data; and determine cerebral perfusion state types to which the sensitive brain regions belong according to the blood perfusion characteristics of the sensitive brain regions and blood flow perfusion characteristic thresholds corresponding to the cerebral perfusion state types.

Optionally, it is hypothesized that the cervical blood flow data include first cervical blood flow data in a first state and second cervical blood flow data in a second state.

It is hypothesized that the transceiving module 101 is further configured to receive cerebral perfusion data from a cerebral perfusion data acquisition device, and the cerebral perfusion data include qBOLD data.

It is hypothesized that qBOLD data of any brain region in the plurality of brain regions include first qBOLD data of the brain region in the first state, and second qBOLD data of the brain region in the second state.

Based on the above hypotheses, for any brain region, when creating a mapping relationship between cervical blood flow data and sensitive brain regions in a plurality of brain regions, the processor 102 is further configured to:

acquire a cervical blood flow difference between the first cervical blood flow data and the second cervical blood flow data; acquire a BOLD difference between the first qBOLD data and the second qBOLD data; calculate a dynamic time warping distance sequence of the cervical blood flow difference and the BOLD difference; take brain regions corresponding to peak values and/or trough values in the dynamic time warping distance sequence of the cervical blood flow difference and the BOLD difference as sensitive brain regions, and construct a mapping relationship between the cervical blood flow data and the sensitive brain regions.

Figure 6:
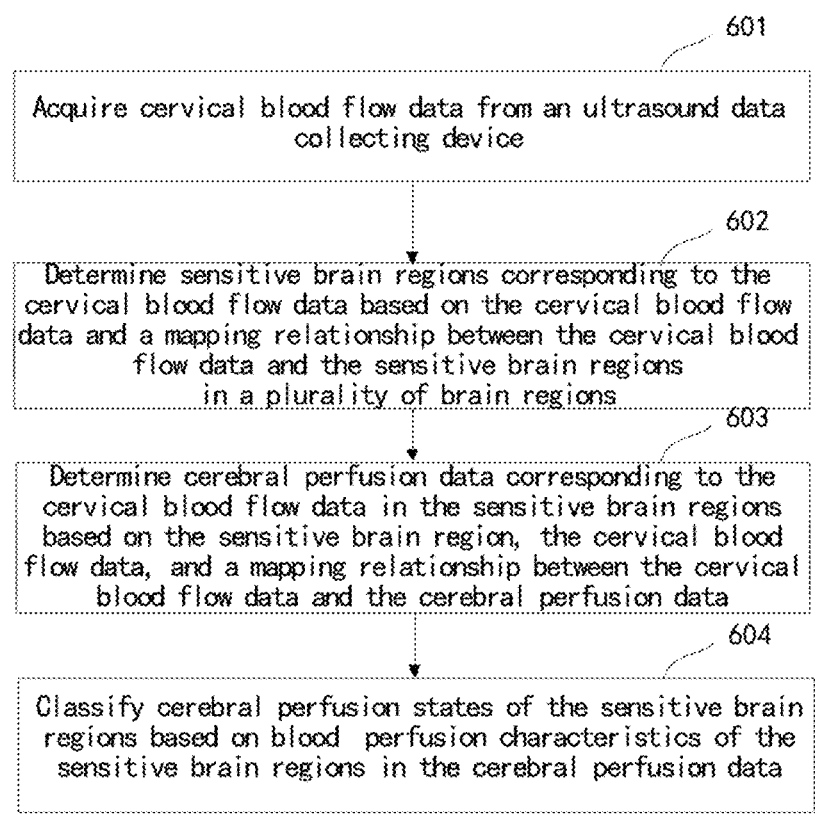
FIG. 6 is a schematic diagram of another cerebral perfusion state classification method according to embodiments of the present application.

It is worthwhile to note that the cerebral perfusion state classification apparatus is similar to the implementation modes of another cerebral perfusion state classification apparatus corresponding to FIG. 1 that is described above, and the similarities refer to the above, and will not be described here FIG. 6 is a schematic flowchart of a cerebral perfusion state classification method according to an embodiment of the present application. The method specifically includes the following steps.

At step 601, cervical blood flow data are acquired from an ultrasound data collecting device.

At step 602, sensitive brain regions corresponding to the cervical blood flow data are determined based on the cervical blood flow data and a mapping relationship between the cervical blood flow data and the sensitive brain regions in a plurality of brain regions.

At step 603, cerebral perfusion data corresponding to the cervical blood flow data in the sensitive brain regions based on the sensitive brain regions, the cervical blood flow data, and a mapping relationship between the cervical blood flow data and the cerebral perfusion data.

At step 604, cerebral perfusion states of the sensitive brain regions are classified based on blood perfusion characteristics of the sensitive brain regions in the cerebral perfusion data.

It is worthwhile to note that the cerebral perfusion state classification method is similar to the implementation modes of the cerebral perfusion state classification apparatus provided in FIG. 1, and the similarities refer to the above, and will not be described here.

Figure 7:
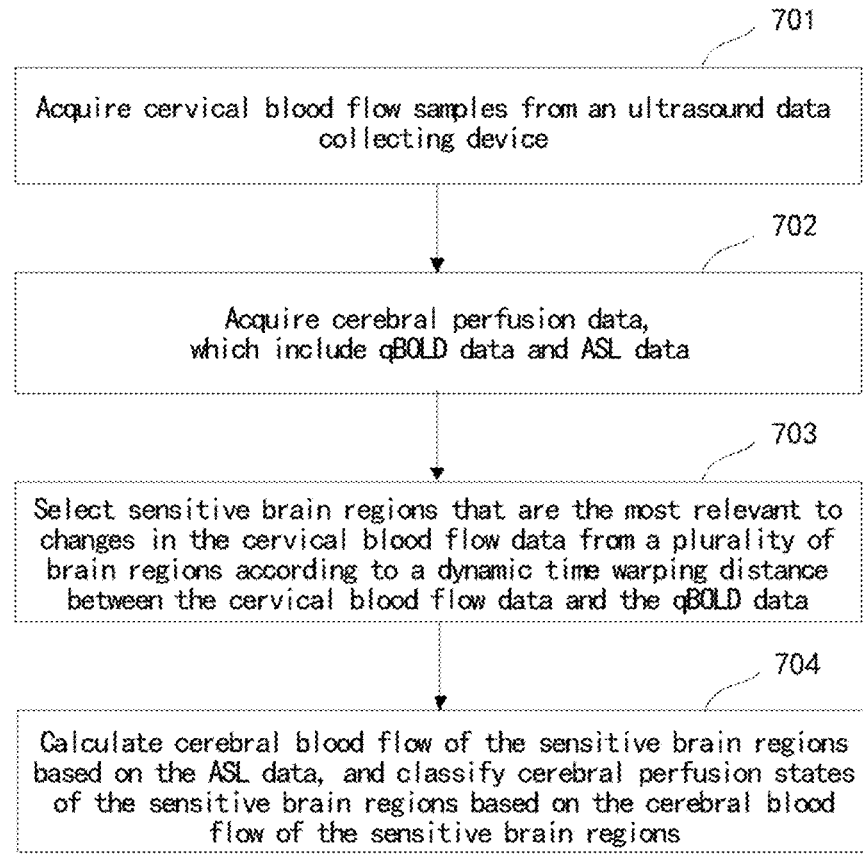
FIG. 7 is a schematic flowchart of a method for training a cerebral perfusion state classification model according to embodiments of the present application.

FIG. 7 is a schematic flowchart of a method for training a cerebral perfusion state classification model according to an embodiment of the present application. As shown in FIG. 7, the method includes the following steps.

At step 701, cervical blood flow data are acquired from an ultrasound data collecting device.

At step 702, cerebral perfusion data are acquired from a cerebral perfusion data acquisition device. The cerebral perfusion data include qBOLD data and ASL data.

At step 703, sensitive brain regions that are the most relevant to changes in the cervical blood flow data are selected from a plurality of brain regions according to a dynamic time warping distance between the cervical blood flow data and the qBOLD data.

At step 704, cerebral blood flow of the sensitive brain regions is calculated based on the ASL data, and cerebral perfusion states of the sensitive brain regions are classified according to the cerebral blood flow of the sensitive brain regions.

Optionally, cerebral blood flow thresholds are preset in the sensitive brain regions. By comparing actual cerebral blood flow of the sensitive brain regions to the cerebral blood flow thresholds, the cerebral perfusion states of the sensitive brain regions can be classified. A specific implementation mode refers to the relevant description of the above embodiments.

It is worthwhile to note that the implementation principle of the cerebral perfusion state model trained by the above method is similar to the implementation principle of the cerebral perfusion state classification apparatus provided in FIG. 1, and the similarities refer to the above, and will not be described here.

Figure 8:
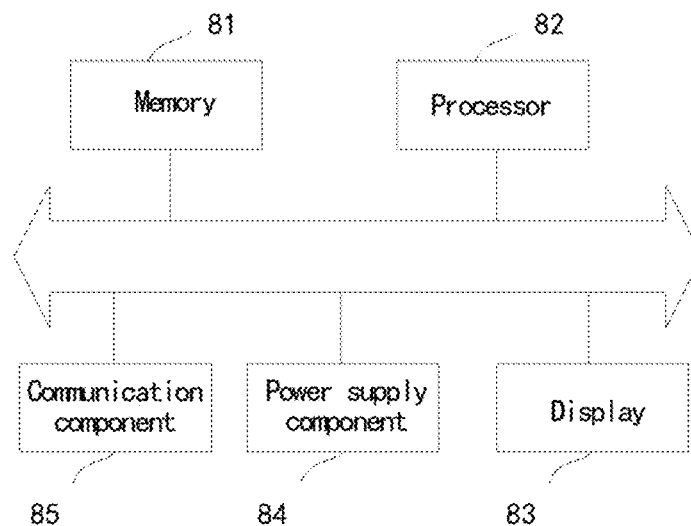
FIG. 8 is a schematic structural diagram of another electronic device according to embodiments of the present application.

FIG. 8 is a schematic structural diagram of an electronic device according to an embodiment of the present application. As shown in FIG. 8, the electronic device includes: a memory 81 and a processor 82, wherein the memory 81 is configured to store a program; and
the processor 82 is coupled with the memory and configured to execute the program stored in the memory so as to:
acquire cervical blood flow data from an ultrasound data collecting device;
determine sensitive brain regions corresponding to the cervical blood flow data based on the cervical blood flow data and a mapping relationship between the cervical blood flow data and the sensitive brain regions in a plurality of brain regions;
determine cerebral perfusion data corresponding to the cervical blood flow data in the sensitive brain regions based on the sensitive brain regions, the cervical blood flow data, and a mapping relationship between the cervical blood flow data and the cerebral perfusion data; and
classify cerebral perfusion states of the sensitive brain regions based on blood perfusion characteristics of the sensitive brain regions in the cerebral perfusion data.

The above memory 81 can be configured to store other data so as to support the operation on a computer device. Examples of these data include any application program or instruction of methods that are operated on the computer device. The memory 81 can be implemented by any type of volatile or non-volatile storage device or a combination thereof, such as a static random access memory (SRAM), an electrically erasable programmable read-only memory (EEPROM), an erasable programmable read-only memory (EPROM), a programmable read only memory (PROM), a read-only memory (ROM), a magnetic storage, a flash memory, a magnetic disk, and an optical disk.

When executing the program in the memory 81, the processor 82 can also realize other functions in addition to the above functions, which specifically refers to the description of various foregoing embodiments.

Further, as shown in FIG. 8, the electronic device also includes other components such as a display 83, a power supply component 84, and a communication component 85. Some components are schematically shown in FIG. 8, and the electronic device may include other components in addition to the components shown in FIG. 8.

Accordingly, an embodiment of the present application also provides a readable storage medium storing a computer program that, when being executed by a computer, implements the steps or functions of the cerebral perfusion state classification methods provided in various above embodiments.

The above apparatus embodiments are only exemplary, in which the units described as separate components may or may not be physically separated, and the components displayed as units may or may not be physical units, that is, they may be located in the same place, or can be distributed over a plurality of network units. Some or all of the modules may be selected according to actual needs to achieve the purpose of the solution of the embodiments. Those of ordinary skill in the art can understand and implement the embodiments without involving any creative effort.

Based on the description of the above implementation modes, those skilled in the art can clearly understand that each implementation mode can be implemented by means of software plus a necessary general hardware platform, and certainly can also be implemented by hardware. Based on this understanding, the essence of the above technical solutions or the part that makes contributions to the prior art can be embodied in the form of software product, and the computer software product can be stored in a computer-readable storage media, such as ROM/RAM, a magnetic disk, and an optical disc, and includes several instructions for causing a computer device (may be a personal computer, a server or a network device) to perform the methods described in the embodiments or some parts of the embodiments.

Finally, it should be noted that the above embodiments are only used to describe the technical solutions of the present application, but are not intended to limit the present application. Although the present application has been described in detail with reference to the foregoing embodiments, those of ordinary skill in the art should understand that: the technical solutions described in the foregoing embodiments can be still modified, or some technical features are equivalently replaced; and these modifications or replacements do not make the essence of the corresponding technical solutions deviate from the spirit and scope of the technical solutions in the embodiments of the present application.

What is claimed is:

1. A cerebral perfusion state classification apparatus, comprising:
   a transceiving module, configured to acquire cervical blood flow data from an ultrasound data collecting device; and
   a processor, configured to determine cerebral perfusion data corresponding to the cervical blood flow data based on the cervical blood flow data and a mapping relationship between the cervical blood flow data and the cerebral perfusion data; and
   also configured to classify cerebral perfusion states of a plurality of brain regions based on blood perfusion characteristics of the plurality of brain regions in the cerebral perfusion data, wherein classifying cerebral perfusion states of a plurality of brain regions based on blood perfusion characteristics of the plurality of brain regions in the cerebral perfusion data comprises extract blood perfusion characteristics of a plurality of brain regions from the cerebral perfusion data; and
   determine a cerebral perfusion state type to which each of the plurality of brain regions belongs based on the blood perfusion characteristics and blood perfusion characteristic thresholds corresponding to cerebral perfusion state types; and
   wherein when determining cerebral perfusion data corresponding to the cervical blood flow data based on the cervical blood flow data and a mapping relationship between the cervical blood flow data and the cerebral perfusion data, the processor is specifically configured to:
   extract cervical blood flow characteristics from the cervical blood flow data; and
   input the cervical blood flow characteristics into a pre-trained network model to obtain cerebral perfusion data corresponding to the cervical blood flow characteristics,
   wherein the network model is trained based on cervical blood flow characteristic samples and cerebral perfusion data samples;
   wherein the network model comprises: a Seq2Seq model comprising an encoder and a decoder constructed based on long short-term memory (LSTM);
   the network model further comprises: a forget gate ($f_t$), an input gate ($i_t$), and an output gate ($o_t$);
   the forget gate ($f_t$) is realized as: $f_t = \sigma(w_f \cdot h_{t-1} + u_f \cdot x_t + b_f)$; $x_t$ is a current input, $h_{t-1}$ is a previous output,
   the input gate ($i_t$) is realized as: $i_t = \sigma(w_i \cdot h_{t-1} + u_i \cdot x_t + b_i)$, $\tilde{c}_t = \tan h(w_c \cdot h_{t-1} + u_c \cdot x_t + b_c)$, and $c_t = f_t \odot C_t + i_t \odot \tilde{C}_t$; $C_t$ is a current cell state, $\tilde{C}_t$ is a new information; and
   the output gate $o_t$ is realized as: $o_t = \sigma(w_o \cdot h_{t-1} + u_o \cdot x_t + b_o)$, and $h_t = o_t \tan h \odot (C_t)$.

2. The apparatus according to claim 1, wherein the processor is further configured to:
   receive a brain magnetic resonance image obtained by arterial spin labeling;
   divide the brain magnetic resonance image into a plurality of brain regions; and
   take cerebral perfusion data of each of the plurality of brain regions as the cerebral perfusion data samples.

3. The apparatus according to claim 1, wherein the network model comprises: a Seq2Seq model comprising an encoder and a decoder;
   and the Seq2Seq model comprises: an encoder and a decoder that are constructed based on long short-term memory (LSTM).

4. The apparatus according to claim 1, wherein the blood perfusion characteristics comprise cerebral blood flow; and
   the processor is further configured to: set cerebral blood flow thresholds corresponding to the cerebral perfusion state types.

5. The apparatus according to claim 1, wherein the cervical blood flow data comprise one or a combination of: cervical vessel blood flow data and vascular lumen morphology change data.

6. A cerebral perfusion state classification method, comprising:
   acquiring cervical blood flow data from an ultrasound data collecting device;
   determining cerebral perfusion data corresponding to the cervical blood flow data based on the cervical blood flow data and a mapping relationship between the cervical blood flow data and the cerebral perfusion data; and
   classifying cerebral perfusion states of a plurality of brain regions based on blood perfusion characteristics of the plurality of brain regions in the cerebral perfusion data, wherein classifying cerebral perfusion states of a plurality of brain regions based on blood perfusion characteristics of the plurality of brain regions in the cerebral perfusion data comprises extracting blood perfusion characteristics of a plurality of brain regions from the cerebral perfusion data; and determining a cerebral perfusion state type to which each of the plurality of brain regions belongs based on the blood perfusion characteristics and blood perfusion characteristic thresholds corresponding to cerebral perfusion state types; and wherein when determining cerebral perfusion data corresponding to the cervical blood flow data based on the cervical blood flow data and a mapping relationship between the cervical blood flow data and the cerebral perfusion data, the method further comprises:

extracting cervical blood flow characteristics from the cervical blood flow data; and inputting the cervical blood flow characteristics into a pre-trained network model to obtain cerebral perfusion data corresponding to the cervical blood flow characteristics, wherein the network model is trained based on cervical blood flow characteristic samples and cerebral perfusion data samples;

wherein the network model comprises: a Seq2Seq model comprising an encoder and a decoder constructed based on long short-term memory (LSTM);

the network model further comprises: a forget gate ($f_t$), an input gate ($i_t$), and an output gate ($o_t$);

the forget gate ($f_t$) is realized as: $f_t = \sigma(w_f \cdot h_{t-1} + u_f \cdot x_t + b_f)$; $x_t$ is a current input, $h_{t-1}$ is a previous output, the input gate ($i_t$) is realized as: $i_t = \sigma(w_i \cdot h_{t-1} + u_i \cdot x_t + b_i)$, $\tilde{c}_t = \tan h(w_c \cdot h_{t-1} + u_c \cdot x_t + b_c)$, and $c_t = f_t \odot C_t + i_t \odot \tilde{C}_t$; $C_t$ is a current cell state, $\tilde{C}_t$ is a new information; and the output gate $o_t$ is realized as: $o_t = \sigma(w_o \cdot h_{t-1} + u_o \cdot x_t + b_o)$, and $h_t = o_t \tan h \odot (C_t)$.

7. An electronic device, comprising: a memory and a processor, wherein, the memory is configured to store a program; and the processor is coupled with the memory and configured to execute the program stored in the memory so as to:

acquire cervical blood flow data from an ultrasound data collecting device;

determine cerebral perfusion data corresponding to the cervical blood flow data based on the cervical blood flow data and a mapping relationship between the cervical blood flow data and the cerebral perfusion data; and classify cerebral perfusion states of a plurality of brain regions based on blood perfusion characteristics of the plurality of brain regions in the cerebral perfusion data, wherein classifying cerebral perfusion states of a plurality of brain regions based on blood perfusion characteristics of the plurality of brain regions in the cerebral perfusion data comprises extract blood perfusion characteristics of a plurality of brain regions from the cerebral perfusion data; and determine a cerebral perfusion state type to which each of the plurality of brain regions belongs based on the blood perfusion characteristics and blood perfusion characteristic thresholds corresponding to cerebral perfusion state types; and wherein when determining cerebral perfusion data corresponding to the cervical blood flow data based on the cervical blood flow data and a mapping relationship between the cervical blood flow data and the cerebral perfusion data, the processor is specifically configured to:

extract cervical blood flow characteristics from the cervical blood flow data; and input the cervical blood flow characteristics into a pre-trained network model to obtain cerebral perfusion data corresponding to the cervical blood flow characteristics, wherein the network model is trained based on cervical blood flow characteristic samples and cerebral perfusion data samples;

wherein the network model comprises: a Seq2Seq model comprising an encoder and a decoder constructed based on long short-term memory (LSTM);

the network model further comprises: a forget gate ($f_t$), an input gate ($i_t$), and an output gate ($o_t$);

the forget gate ($f_t$) is realized as: $f_t = \sigma(w_f \cdot h_{t-1} + u_f \cdot x_t + b_f)$; $x_t$ is a current input, $h_{t-1}$ is a previous output, the input gate ($i_t$) is realized as: $i_t = \sigma(w_i \cdot h_{t-1} + u_i \cdot x_t + b_i)$, $\tilde{c}_t = \tan h(w_c \cdot h_{t-1} + u_c \cdot x_t + b_c)$, and $c_t = f_t \odot C_t + i_t \odot \tilde{C}_t$; $C_t$ is a current cell state, $\tilde{C}_t$ is a new information; and the output gate $o_t$ is realized as: $o_t = \sigma(w_o \cdot h_{t-1} + u_o \cdot x_t + b_o)$, and $h_t = o_t \tan h \odot (C_t)$.

8. A non-transitory computer storage medium, configured to store a computer program that, when executed on a computer, performs the following method:

acquiring cervical blood flow data from an ultrasound data collecting device;

determining cerebral perfusion data corresponding to the cervical blood flow data based on the cervical blood flow data and a mapping relationship between the cervical blood flow data and the cerebral perfusion data; and classifying cerebral perfusion states of a plurality of brain regions based on blood perfusion characteristics of the plurality of brain regions in the cerebral perfusion data, wherein classifying cerebral perfusion states of a plurality of brain regions based on blood perfusion characteristics of the plurality of brain regions in the cerebral perfusion data comprises extracting blood perfusion characteristics of a plurality of brain regions from the cerebral perfusion data; and determining a cerebral perfusion state type to which each of the plurality of brain regions belongs based on the blood perfusion characteristics and blood perfusion characteristic thresholds corresponding to cerebral perfusion state types; and wherein when determining cerebral perfusion data corresponding to the cervical blood flow data based on the cervical blood flow data and a mapping relationship between the cervical blood flow data and the cerebral perfusion data, the method further comprises:

extracting cervical blood flow characteristics from the cervical blood flow data; and inputting the cervical blood flow characteristics into a pre-trained network model to obtain cerebral perfusion data corresponding to the cervical blood flow characteristics, wherein the network model is trained based on cervical blood flow characteristic samples and cerebral perfusion data samples;

wherein the network model comprises: a Seq2Seq model comprising an encoder and a decoder constructed based on long short-term memory (LSTM);

the network model further comprises: a forget gate ($f_t$), an input gate ($i_t$), and an output gate ($o_t$);

the forget gate ($f_t$) is realized as: $f_t = \sigma(w_f \cdot h_{t-1} + u_f \cdot x_t + b_f)$; $x_t$ is a current input, $h_{t-1}$ is a previous output, the input gate ($i_t$) is realized as: $i_t = \sigma(w_i \cdot h_{t-1} + u_i \cdot x_t + b_i)$, $\tilde{c}_t = \tan h(w_c \cdot h_{t-1} + u_c \cdot x_t + b_c)$, and $c_t = f_t \odot C_t + i_t \odot \tilde{C}_t$; $C_t$ is a current cell state, $\tilde{C}_t$ is a new information; and the output gate $o_t$ is realized as: $o_t=\sigma(w_o \cdot h_{t-1}+u_o \cdot x_t+b_o)$, and $h_t=o_t \tan h \odot (C_t)$.

* * * * *